United States Patent [19]
Draenert

[11] Patent Number: 5,507,749
[45] Date of Patent: Apr. 16, 1996

[54] SEALING DEVICE FOR THE MEDULLARY CAVITY

[76] Inventor: Klaus Draenert, Gabriel-Max-Str. 3, D-8000 München, Germany

[21] Appl. No.: 259,140

[22] Filed: Jun. 13, 1994

Related U.S. Application Data

[63] Continuation of Ser. No. 466,357, filed as PCT/EP89/00794, Jul. 8, 1988, abandoned.

[30] Foreign Application Priority Data

Jul. 8, 1988 [DE] Germany .......................... 38 23 287.1

[51] Int. Cl.⁶ ..................................................... A61F 1/00
[52] U.S. Cl. ................................................. 606/94; 606/92
[58] Field of Search ...................... 606/92, 93, 94, 606/95, 86, 72, 53; 222/542

[56] References Cited

U.S. PATENT DOCUMENTS

| | | | |
|---|---|---|---|
| 1,971,284 | 8/1934 | Stockman | 222/542 |
| 4,205,767 | 6/1980 | Shackelford | 222/542 |
| 4,274,163 | 6/1981 | Malcom et al. | 3/1.91 |
| 4,338,925 | 7/1982 | Miller | 128/92 |
| 4,593,685 | 6/1986 | McKay et al. | 606/92 X |
| 4,595,006 | 6/1986 | Burke et al. | 606/94 |
| 4,671,263 | 6/1987 | Draenert | 128/92 |
| 4,815,454 | 3/1989 | Dozier, Jr. | 128/92 |
| 4,896,662 | 1/1990 | Noble | 606/92 X |
| 4,966,601 | 10/1990 | Draenert | 606/92 |

FOREIGN PATENT DOCUMENTS

| | | |
|---|---|---|
| 0073604 | 8/1982 | European Pat. Off. . |
| 0320138 | 11/1988 | European Pat. Off. . |

OTHER PUBLICATIONS

The Use Of Methylmathacrylate As An Adjunct In Internal Fixation, Harrington et al., Dated Dec. 1972.

*Primary Examiner*—Sam Rimell
*Attorney, Agent, or Firm*—Kinney & Lange

[57] ABSTRACT

The invention relates to a device for sealing the medullary cavity of a bone during the application of bone cement. The device comprises an elastic bottom portion (10) for positive contact with the bone around the medullary cavity and a rigid top portion (30). When the bone cement cartridge (40) is pushed down, the rigid top portion (30) presses the bottom portion (10) against the bone, and the medullary cavity is sealed in a vacuum-tight manner. The device according to the invention makes it easier to fill the medullary cavity with bone cement under vacuum and to carry out drainage at the same time. (FIG. 1).

19 Claims, 2 Drawing Sheets

SEALING DEVICE FOR THE MEDULLARY CAVITY

This is a Continuation of application Ser. No. 07/466,357, filed as PCT/EP89/00794, Jul. 8, 1988, now abandoned.

BACKGROUND OF THE INVENTION

The invention relates to device or for sealing the medullary cavity of a bone when applying bone cement.

In arthroplastic surgery, most implants are anchored in the bony bed with the help of so-called bone cement. This bone cement usually consists of polymethylmethacrylates or related compounds. In order to improve the penetration of the bone cement into the honeycomb structure of the bone marrow, attempts were made to wash the bony bed under pressure and to apply the bone cement under pressure. This technique, which is also called the "high pressurising technique", is mostly used with bone cement of low viscosity.

This technique, however, led to a number of fatal incidents. Both animal experiments and clinical examinations showed that an increase in intramedullary pressure may cause reflex cardiac arrest and give rise to fatal fat and bone marrow embolisms. Furthermore, this method did not succeed in keeping the bony bed clear of blood. Rather, blood flowed into the bony bed in dependence on the blood pressure and blended with the bone cement, thus considerably weakening its material properties. Attempts have already been made to improve the mechanical strength of the bone cement used in clinics by vacuum-mixing it and prepressurising it. It is, however, essential for the strengthened material of the bone cement to be transferred to the bony bed of the patients without any loss of its material properties and without endangering the patients' lives.

Thus a method has been developed with which the bony bed can be kept dry and the cement can be applied in an artefact-free manner, and this without jeopardizing the patient with the temporary increase of the intramedullary pressure. In this method, the bone cement is initially mixed under vacuum and prepressurised and is then applied into the medullary cavity using a bone cement pistol or press as described, for example, in EP-A-170 120 or U.S. Pat. No. 4,671,263. At the same time, a cannulated bone screw is used to apply a vacuum distally. In this way the bone cement is sucked deep into the medullary cavity whilst blood, fat and bone marrow are sucked out of the bone canal at the same time. Once the prosthesis component has been inserted, the vacuum lead is pinched off, whereupon a cannulated bone screw is used to proximally apply a vacuum. This means that the vacuum will remain effective in the metaphysis until the bone cement has hardened. This method is characterised by filling the medullary cavity under vacuum and draining it at the same time. It enables complete and artefact-free application of the bone cement around the prosthesis along with deep penetration of the bone cement into the spongiosa.

In order to maintain the required partial vacuum in the medullary cavity and to prevent the bone cement from seeping out, it is essential to keep the medullary cavity as tightly sealed as possible when applying the bone cement.

This is usually aimed at with a collar placed around the tip of the vessel or cartridge with which the bone cement is applied.

SUMMARY OF THE INVENTION

The object underlying the invention is the provision of a device for sealing the medullary cavity of a bone during the application of bone cement, with which device the medullary cavity can be essentially vacuum-tightly sealed in the region in which the bone cement is applied.

According to the invention, this object is achieved by the device according to the patent claims.

Thus the subject matter of the invention is a kind of medullary cavity seal or a medullary cavity sealing.

The basic idea behind the invention is to provide a device comprising a flexible or soft bottom portion that acts as a packing means and when mechanical pressure is applied thereto, places itself around the opening of the medullary cavity like a packing ring, and a hard or rigid top portion to press the flexible bottom portion against the bone around the medullary cavity, for instance against the resection plane. Thus the bottom portion practically acts as an elastic intermediate and the top portion is a shield with which the intermediate is pressed down, especially in the initial phase of evacuation, until partial vacuum, which seals the bottom portion to the bone, is achieved in the medullary cavity.

The sealing device is preferably pressed down directly by means of the tip of the vessel or cartridge that contains the bone cement. For this purpose, the shape of the interior of the bottom portion and/or top portion of the sealing device is preferably adapted to the shape of the cartridge tip. If the cartridge tip is conically tapered, the interior of the sealing device, preferably of the elastic bottom portion, will too have, at least partially the shape of a conical seat or bearing surface. If the cartridge is cylindrical, it is also preferable for the bearing surface to be cylindrical in shape and have the same or a slightly larger diameter to ensure positive-fit incorporation of the cartridge. When the cartridge is pressed against the sealing device, a practically vacuum-tight seal is formed between the tip of the cartridge and the bearing surface as well as between the lower sealing surface of the sealing device and the bone around the opening of the medullary canal. This permits the build-up of partial vacuum in the medullary cavity and prevents the bone cement from being pushed back out of the medullary cavity. The tip of the cartridge fits into the seat made of silicone rubber. If the tip of the cartridge is received in the hard top portion, vacuum or sealing grease can be applied between the two to seal them.

If the bearing surface of the bottom portion on the bone is a plane surface, such as the resection plane of the femur in hip joint surgery, the lower surface of the bottom portion can also be a plane surface. However, it is preferable for the surface to be convex in shape and to be flat only when it is pressed down. This ensures excellent sealing.

The spongiosa spaces represent funnel systems open at the top. In order to ensure the optimal filling of said spongiosa spaces, the lower surface of the bottom portion of the device comprises a recess or groove. The circumference of the recess is such as to expose as large a portion as possible of the resection plane around the medullary cavity so that the spongiosa can be filled over a large area.

When used in the acetabulum, the bottom portion is preferably to be shaped at least in part as a ball or a packing ring whose dimensions are such that it lies and seals in the supporting roof and not on the rim of the acetabulum. It is especially preferable for the bottom portion to exhibit a hemispherical shell or bowl above the sealing bead, which shell is in positive-fit contact with the equally hemispherical portion of the top portion. In this case, the bottom portion has the shape of a closed inlay. This ensures that any bone cement that is pushed out will only contact the material of the bottom portion and not the top portion.

The bottom portion can either receive the top portion in a slot and/or can lie in a groove of the top portion.

The device according to the invention is generally applicable in all joint replacement operations. Its shape depends on the conditions of each specific application.

It is preferable for the sealing surface of the bottom portion to be essentially annular or bead-shaped or biconvex. The curve of the bottom portion prevents any bends or pleats that could occur in a flat or disc-shaped bottom portion; in this case it would not be possible to ensure clean positioning at the resection plane, and the leak would prevent the formation of sufficient partial vacuum in the medullary cavity.

If possible, the upper surface of the bottom portion and the lower surface of the rigid top portion are adapted to one another to ensure positive fit. This allows the transferral of the pressure applied to the rigid top portion to the bottom portion, thus pressing and sealing it to the bone around the medullary cavity. The bottom portion and the top portion preferably comprise as large a contact surface as possible. Said contact surface can, for example, have the approximate shape of an upwardly tapered semicircular area. If the bottom portion is annular in shape, the lower surface of the top portion preferably comprises an annular groove to receive the bottom portion in a positive-fit manner. It is preferable to provide means to prevent the top and bottom portion from twisting, for example several pins or projections that protrude from the bottom or top portion and fit into recesses of the other portion. The soft bottom portion can also be a complete inlay adapted to the shape of the top portion, for example two hemispherical shells with pins to be mechanically fixed into corresponding recesses. The two portions can also be firmly attached to one another, e.g. glued to one another.

The elastic bottom portion is preferably made of silicone rubber or similar materials as used in vacuum techniques. The upper portion is preferably made of a metal such as aluminium, steel or titanium, or of a hard plastic material such as teflon, TPX or another sterilisable plastic material.

BRIEF DESCRIPTION OF THE DRAWINGS

In the following, the invention will be described in greater detail in conjunction with the drawing. The drawing shows.

DETAILED DESCRIPTION OF THE PREFERRED EMBODIMENTS

Figure 1:
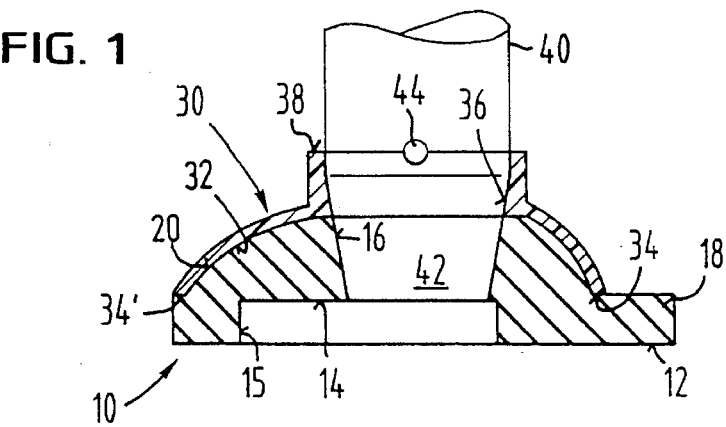
FIG. 1 a cross section along line I—I of FIG. 2 of a device according to the invention to be used for sealing the medullary cavity of the femur, FIG. 2 a top view of the device according to FIG. 1, FIG. 3 a cross section along line III—III of FIG. 4 of a device according to the invention to be used for sealing the acetabulum, FIG. 4 a diagrammatic top view of the device according to FIG. 3 and FIG. 5 a further device according to the invention to be used in the acetabulum.

The sealing device according to FIG. 1 comprises a flexible, soft bottom portion 10 and a hard, rigid top portion 30. Bottom portion 10 comprises an even, lower surface 12 that lies on the resection plane during use. As explained above, the lower sealing surface can also be bead-shaped or convex in order to ensure secure sealing. A recess 14 is provided around a central opening, and the circumferential collar 15 of said recess is approximately oval or elliptic in shape. The dimensions of recess 14 are such that the spongiosa honeycomb structure around the opening of the medullary cavity is exposed, and lower surface 12 only comes into contact with the bone via an outer rim of a few millimeters in width. In this way the exposed spongiosa honeycomb structure can be filled with bone cement. The interior of bottom portion 10 comprises a continuous, downwardly tapering opening with a conical bearing surface or contact surface 16 that surrounds the conical tip of the bone cement cartridge. If the cartridge is pressed against the sealing device, contact surface 16 seals to the tip of the cartridge in a vacuum-tight manner.

To increase the sealing surface and improve stability, bottom portion 10 comprises a projection 18. The upper surface 20 of bottom portion 12 is bead-shaped or spherically curved. This increases the stability when the top portion 30 is pressed against the bottom portion 10.

The lower surface 32 of the top portion 30 is also curved and is positioned in a form-fit manner on the upper surface 20 of the bottom portion 10. The circumferential lower rim 34, 34' of the top portion 30 is also positioned in a formfit manner on a shoulder of the bottom portion 10. The interior of the top portion 30 comprises at its top a straight, cylindrical projection with a conical opening 36 underneath. The upper surface is provided with a rim 38.

FIG. 1 also shows a bone cement cartridge 40 with a conical tip 42 and pins or projections 44. During application, the cartridge 40 is pushed down. The pins 44 abut against the upper rim 38 of the top portion 30 and push the top portion 30 down against the bottom portion 10. If enough pressure is applied, the conical tip 42 and the contact surface 16 are sealed together, as are the lower surface 12 and the bone. This seals the medullary cavity in a practically vacuum-tight manner and prevents the applied bone cement from seeping out. If, for example, the bone cement is proximally applied in the medullary cavity of the femur, the medullary cavity is distally drained with a cannulated bone screw. The proximal seal allows the build-up of a vacuum or partial vacuum in the medullary cavity during bone cement application. This avoids any complications in applying the bone cement under vacuum and carrying out draining at the same time.

Figure 2:
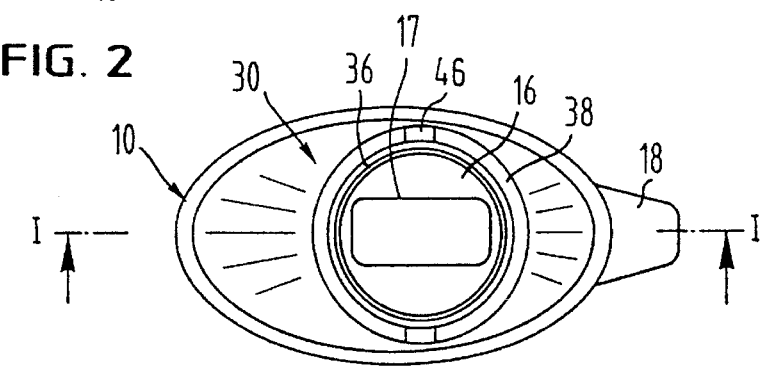

FIG. 2 is a more detailed top view of the device according to FIG. 1, but without the bone cement cartridge. FIG. 2 illustrates the conical contact surface 16 of the bottom portion 10 with its oval opening 17 whose shape is approximately that of the opening of the cartridge tip. The round upper rim 38 surrounds the cylindrical cartridge 40. The cone 36 also matches the shape of the cartridge tip. The rim 38 is provided with two recesses or slots 46 for receiving in a form-fit manner the pins 44 of the cartridge 40, thus ensuring that the cartridge 40 is pressed against the device in a stable manner.

Figure 3:
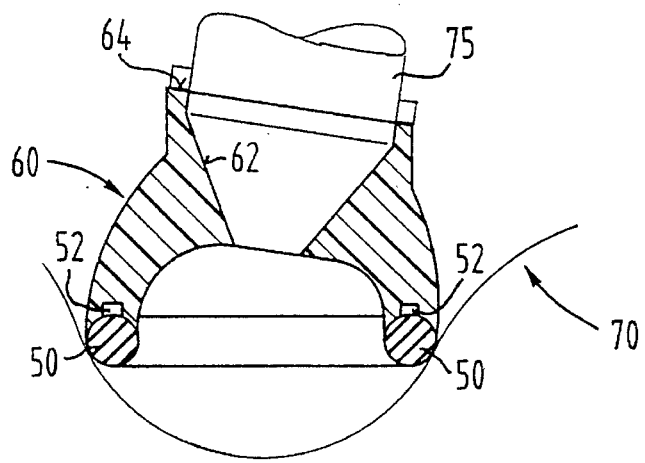

The sealing device according to FIG. 3 for the acetabulum comprises a flexible, soft bottom portion 50 and a rigid top portion 60. The bottom portion 50 is annular in shape and comprises pins or projections 52 that engage in recesses of the top portion 60 to prevent a relative movement between the bottom portion and the top portion. The top portion 60 has the shape of a hollow body whose interior 62 is tapered towards the bottom to receive the tip of the cartridge 75. To improve the seal between the conical contact surface 62 and the cartridge tip, the contact surface 62 may additionally comprise an elastic intermediate layer, which is also cone-shaped. At its top, the top portion 60 comprises a round, circumferential rim 64.

FIG. 3 also diagramatically illustrates the use of the sealing device in an acetabulum 70. The bone cement is in the cartridge 75, which corresponds to the cartridge 40 according to FIG. 1, the cartridge in FIG. 3 having been turned by 90° in comparison to that of FIG. 1. The surgeon presses the conical tip of the cartridge 75 against the inner contact surface 62 of the sealing device, thus pushing it down. This pushes the bottom portion 50, which acts as a packing ring, against the supporting roof of the acetabulum and seals it there in a vacuum-tight manner. The bone cement is then applied from the cartridge 75 in a controlled manner and, at the same time, drainage is applied and the bone cement sucked deep into the spongiosa honeycombs by the forming partial vacuum.

Figure 4:
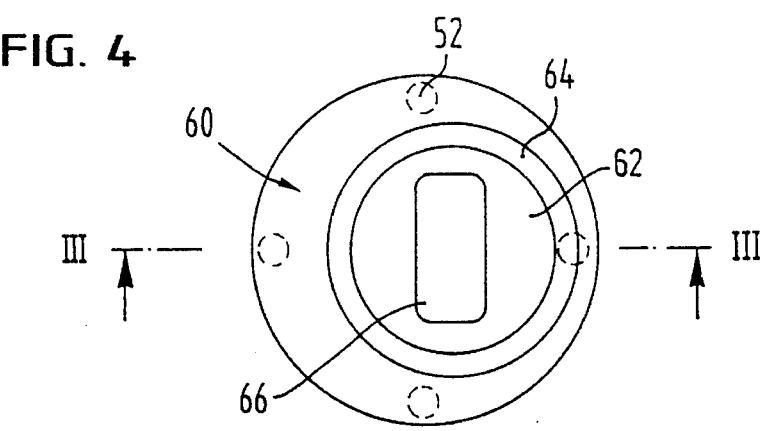

The view of FIG. 4, in which the cartridge has been omitted, shows that the oval opening of the interior 62 of the top portion 60, which receives the cartridge tip, and the rim 64 are not totally symmetric with the sealing bottom portion 50. FIG. 4 also diagramatically shows the four pins 52 of the bottom portion 50.

Figure 5:
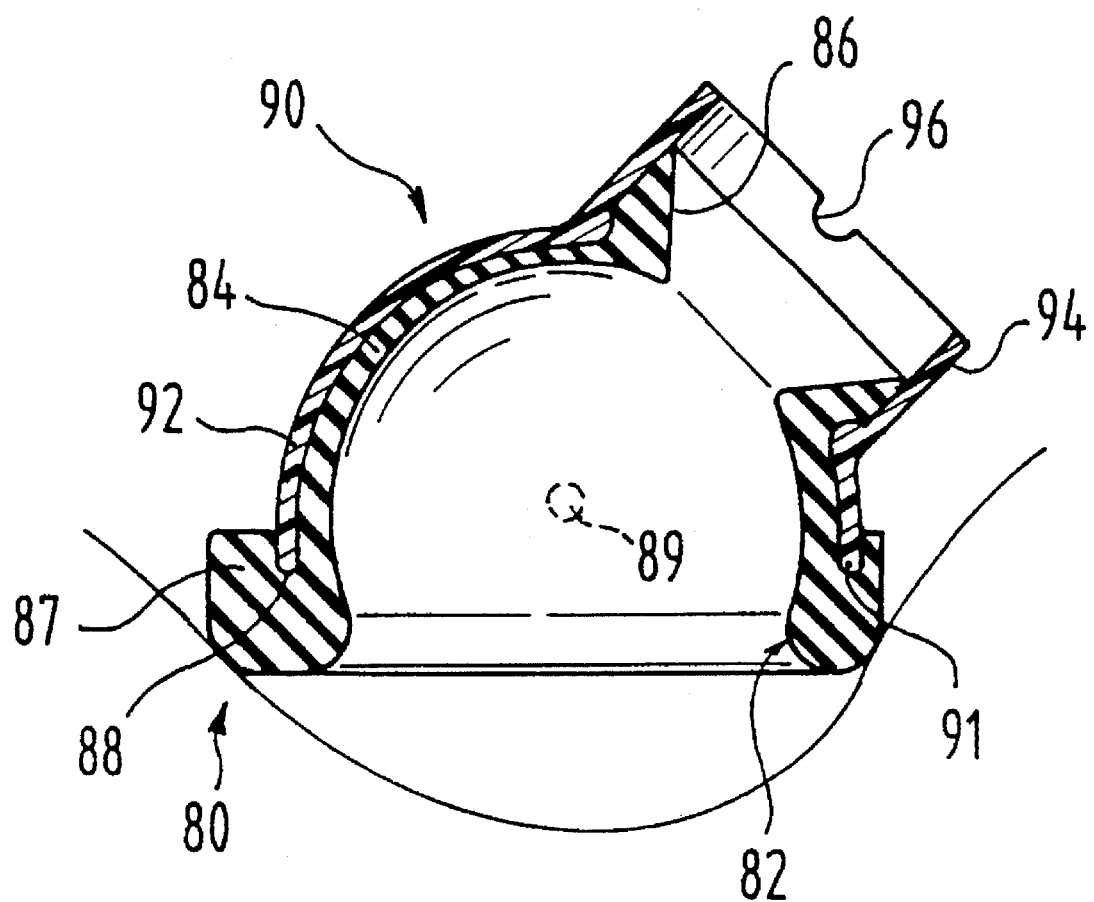

FIG. 5 shows a similar sealing device for the acetabulum to that of FIG. 3. In the sealing device according to FIG. 5, the flexible, soft bottom portion 80 comprises an approximately hemispherical shell or bowl 84 and a member 86 for receiving the cartridge tip in addition to a ring or bead 82, which is similar to the bottom portion 50 according to FIG. 3. The annular or bead-shaped portion 82 may comprise a shoulder 87 that serves to improve stability and to improve sealing by adapting itself to the shape of the acetabulum. A circumferential groove 88 is provided between the annular portion 82 and the hemispherical shell 84. The lower rim 91 of the rigid top portion 90 fits into the groove 88. To prevent a relative twist between the bottom portion 80 and the top portion 90, the bottom portion 80 is provided with several pins or projections 89 that engage with complementary recesses in the top portion 90. The top portion 90 essentially comprises a hemispherical shell 92 and a connection piece 94 that surround the hemispherical shell 84 of the bottom portion and the receiving member 86 of the bottom portion, respectively, in a positive fit manner. As can be taken from FIG. 5, the member for receiving the bone cement cartridge has a lateral position at an angle of about 30° to 60°, preferably 45°, based on the plane formed by the lower packing ring 82. This makes it easier to place the cartridge in position and work with it during surgery.

The upper rim of the top portion 90 comprises several recesses 96, preferably two, for receiving the pins arranged on the cartridge.

The use of the sealing device according to FIG. 5 corresponds to that according to FIG. 3. The surgeon presses the conical tip of the cartridge (not illustrated in FIG. 5) against the conical surface 86, with the upper rim of the top portion and the recesses 96 serving as a stopper for the cartridge and the pins, respectively. This presses the ring 82 of the bottom portion 80 against the supporting roof of the acetabulum where it seals in a vacuum-tight manner whilst the bone cement is being applied from the cartridge.

I claim:

1. A device for sealing a medullary cavity of a bone during the vacuum-application of bone cement, comprising:

an elastic bottom portion having means thereon for removably contacting the bone and providing a partial vacuum seal around the medullary cavity during the vacuum-application of bone cement and for releasing the bottom portion from the bone after the application of the bone cement, the bottom portion having an opening therethrough for applying bone cement to the medullary cavity, and the bottom portion having a section curved upwardly in a direction away from the medullary cavity when positioned thereon such that pressing the curved section seals the bottom portion to the bone; and a rigid top portion fixedly attached to the curved section for pressing the elastic bottom portion against the bone, the top portion having an opening therethrough in communication with the opening of the bottom portion for applying the bone cement;

wherein the top portion and the bottom portion are removable from the medullary cavity after the application of the bone cement.

2. The device according to claim 1, wherein the bottom portion and the top portion each have a shape selected from the group consisting of hollow-cylindrical, annular, semi-circular or ellipsoidal.

3. The device according to claim 1, wherein a lower surface of the bottom portion is adapted to the shape of a resection plane of the bone to be pressed against the bone.

4. The device according to claim 1, wherein at least part of the bottom portion has the shape of a packing ring or a bead.

5. The device according to claim 1, wherein the bottom portion and the top portion are in contact with one another over a curved area.

6. The device according to claim 1, wherein an interior of an underside of the bottom portion comprises a recess whose surface is larger than an opening of the medullary cavity.

7. The device according to claim 1, having means to prevent twisting between the bottom portion and the top portion.

8. The device according to claim 1, wherein the bottom portion and the top portion are firmly connectable.

9. The device according to claim 1, wherein the bottom portion is made of silicone rubber.

10. The device according to claim 1, wherein the top portion is made of a sterilisable plastic material.

11. The device according to claim 2, wherein an interior of the bottom portion has a bearing surface for positively receiving a tip of a container out of which the bone cement is applied.

12. The device according to claim 2, wherein a interior of the top portion has a bearing surface for positively receiving a tip of a container out which the bone cement is applied.

13. The device according to claim 1, wherein the top portion is curved upwardly is a shell-like shape and positioned against the curved section of the bottom portion.

14. The device according to claim 1, wherein the bottom and top portions comprise a common opening for applying bone cement.

15. The device according to claim 14, wherein the common opening is at least partially conical.

16. The device according to claim 1, wherein the bottom portion is the most distal part of the sealing device.

17. The device according to claim 1, wherein the top portion is made of metal.

18. The device according to claim 1, wherein the top portion is made of TPX.

19. The device according to claim 1, wherein the bottom portion provides a vacuum-tight contact with the bone.

* * * * *

UNITED STATES PATENT AND TRADEMARK OFFICE
CERTIFICATE OF CORRECTION

PATENT NO. : 5,507,749
DATED : April 16, 1996
INVENTOR(S) : KLAUS DRAENERT

It is certified that error appears in the above-indentified patent and that said Letters Patent is hereby corrected as shown below:

On title page, item [63] "Related U.S. Application Data", delete

"Jul, 8, 1988", insert --Jul. 10, 1989--

Col. 2, line 37, delete "in-the", insert --in the--

Col. 6, line 47, after "out", insert --of--

Signed and Sealed this

Twenty-third Day of July, 1996

Attest:

BRUCE LEHMAN

Attesting Officer        Commissioner of Patents and Trademarks